(12) United States Patent
Meier et al.

(10) Patent No.: US 6,275,776 B1
(45) Date of Patent: Aug. 14, 2001

(54) METHOD FOR CHARACTERIZING RESIDUAL CRUDE OIL AND PETROLEUM FRACTIONS

(75) Inventors: Paul F. Meier; Dhananjay B. Ghonasgi, both of Bartlesville, OK (US); Michael Wardinsky, Lake Jackson, TX (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/261,714

(22) Filed: Mar. 3, 1999

(51) Int. Cl.$^7$ .............................. G01N 31/00; G06F 19/00
(52) U.S. Cl. ............... 702/27; 208/112; 208/78; 208/46; 208/113
(58) Field of Search .................. 702/27, 30; 208/46, 208/112, 78, 113

(56) References Cited

U.S. PATENT DOCUMENTS

| | | | |
|---|---|---|---|
| 5,158,670 | * 10/1992 | Cody et al. | 208/120 |
| 5,712,797 | 1/1998 | Descales et al. | 364/499 |
| 5,730,859 | 3/1998 | Johnson et al. | 208/78 |
| 5,841,678 | * 11/1998 | Hasenberg et al. | 703/10 |
| 6,071,402 | * 5/2000 | Danot et al. | 208/112 |

\* cited by examiner

*Primary Examiner*—Kamini Shah
*Assistant Examiner*—Demetrius Pretlow
(74) *Attorney, Agent, or Firm*—George E. Bogatie

(57) ABSTRACT

A method to rapidly characterize the hydrocarbon chemistry of heavy residual petroleum mixtures uses three model equations for predicting aromatic carbon content, aromatic hydrogen content and total hydrogen content of the heavy residual oil. The predictive equations are based on three easily measured bulk properties including refractive index, specific gravity and the Watson K factor.

6 Claims, No Drawings

METHOD FOR CHARACTERIZING RESIDUAL CRUDE OIL AND PETROLEUM FRACTIONS

This invention relates to fluidized catalytic cracking (FCC) of hydrocarbon feed stocks, and more particularly to an improved method to accurately predict characterizing chemistry of heavy residual oils and petroleum mixtures used for FCC feed stocks.

BACKGROUND OF THE INVENTION

Fluidic catalytic cracking continues to be the largest catalytic process in the world, and planning of FCC feed stock allocations continues to be a very complex problem, which must be addressed by petroleum refiners. For example, feeds of high economic opportunity are often heavy oils that require specialized FCC processing including a particular set of operating conditions that will realize a profitable product slate. Understanding the feed chemistry of petroleum crude oils and refinery streams has been a very important research topic for many years. Since FCC processes involve manipulation of carbon and hydrogen bonds, an accurate understanding of the feed composition and chemistry would allow the refiner to control operations involving catalytic and non-catalytic reactions. Ideally, the refiner would divide the feed into individual molecular components, however, petroleum FCC feeds are far too complex, such that the amount of analytic effort would be prohibitive.

Many methods have been suggested in the literature for characterization of petroleum feed stocks. Some researchers combine bulk analytical tests into correlating parameters. For example, the Viscosity Gravity Constant (J. B. Hill and H. B. Coats, Ind. Eng. Chem., 20, 641, 1928) is one such correlating parameter. As the name implies, the parameter uses specific gravity and Saybolt viscosity to characterize the oil. Another early parameter is the Watson K factor (K. M. Watson and E. F. Nelson, Ind. Eng. Chem., 25, 880, 1933), which is the cube root of the mean average boiling point divided by the specific gravity. For a given carbon number, the boiling point and specific gravity increase going from paraffins to naphthenes to aromatics, however, specific gravity increases more rapidly, such that high Watson K factors (greater than 12) correspond to an oil with high paraffinic content and low Watson K factor (less than 12) corresponds to an oil with higher aromatic content.

Riazi and Daubert (M. R. Riazi and T. E. Daubert, Ind. Eng. Chem. Proc. Des., Dev., 19, 289, 1980) showed that the Watson K factor is inadequate for the complete differentiation of molecular types, and developed a method to predict molecular composition of petroleum fractions using refractive index, Saybolt viscosity, and specific gravity. This method, which characterizes petroleum oils by molecular types rather than carbon content, is the standard given in the API Technical Data Book "Petroleum Refining," Chapter 2. B.4, (Report No. API-1-80, Apr. 18, 1980). The addition of refractive index complements the other types of tests and helps to better differentiate aromatic, paraffinic, and naphthinic compounds.

For a process such as catalytic cracking, which involves the breaking of carbon-carbon and carbon-hydrogen bonds, characterization of oils by carbon and hydrogen content is more useful than by molecular types. Two common methods used for characterizing the oil in this manner are the n-d-M method (ASTM D3238-80) and a method known as the Total method published by H. Dhulesia (Oil and Gas Journal, 51–54, Jan. 13, 1986). Both of these methods use refractive index as a key correlating property. The data used to develop the n-d-M method were obtained from fractions of five crudes, boiling between 480 and 890° F. (see "Aspects of the Constitution of Mineral Oils," K. van Nes and H. A. van Westen, Elsevier Publishing Co., 1951). The Total method used thirty-three different FCC feed stocks which included some residual oil blends.

Although the above described methods have the advantage of characterizing FCC feeds by carbon and hydrogen content, they experience the objectional feature of being applicable for material boiling at temperatures less than 1000° F.

Accordingly, it is an object of this invention to rapidly characterize potential heavy FCC feed stocks by carbon and hydrogen content.

It is a more specific object of this invention to analyze FCC feed quality for use in a model for computer simulation of an FCC reaction that predicts product yields.

It is a still more specific object to analyze FCC feeds in a simple and efficient manner, which can be routinely carried out in a refinery laboratory.

Still another objective of this invention is to develop a robust feed chemical analysis which is not dependent on feed source or pretreatment.

SUMMARY OF THE INVENTION

According to this invention, the foregoing and other objectives and advantages are achieved in a method for analyzing a mixture of heavy hydrocarbon oils to determine the aromatic carbon content, aromatic hydrogen content, and total hydrogen content of the oil. The method uses three mathematical model equations based on three bulk properties of the oil, and these properties have individual limiting values for infinitely long carbon/hydrogen groups in the liquid state. The petroleum oil properties are refractive index, specific gravity, and the Watson K factor, and the model equations include the respective limiting values.

In a preferred embodiment, the carbon and hydrogen content of oils with boiling points up to 1400° F. is determined from measurements including: refractive index, API gravity, and simulated distillation. The mathematical model equations, which include the limiting value associated with the property, are as follows:

$$C_a = 134.4679[RI - 1.4750] - 20.4858[K - 12.5] \quad \text{EQ. (1)}$$

$$H_a = 333.471[RI - 1.4750]^2 - 6.687[K - 12.5] \quad \text{EQ. (2)}$$

$$H = -20.77[Sp.Gr. - 0.8510] + 0.58[K - 12.5] + 14. \quad \text{EQ. (3)}$$

where:
$C_a$=wt. % aromatic carbon
$H_a$=wt. % aromatic hydrogen
H=wt. % total hydrogen
K=Watson K factor, i.e., $[(VABP(F) + 460)^{1/3}]/Sp.Gr.$
RI=refractive index at 68° F.
SpGr.=specific gravity, density of oil at 60° F. relative to water at 60° F., and VABP = volume average of distillation curve boiling points at % off
= [10% + 30% + 50% + 70% + 90%]/5

The method of this invention using easily measured bulk properties to characterize the hydrocarbon chemistry of a broad spectrum of heavy hydrocarbon oils is advantageous for use in a refinery on a daily basis to aid in optimizing selection of oils for processing in an FCC unit.

Still other objects and advantages of the present invention will become readily apparent to those skilled in the art from the following detailed description, wherein there is shown and described only the preferred embodiments of this invention.

DETAILED DESCRIPTION OF THE INVENTION

The optimum selection of feed stocks, which is usually based on the prediction of product yields from available candidate oils, first requires complex characterization of aliphatic hydrocarbons as well as aromatic hydrocarbons in the feed, wherein the feed characterization is a major input to a computer simulation program that predicts FCC product yields. For the computer simulation of a cracking reaction, it is highly desirable to be able to characterize the chemical nature of wide range of FCC feeds in a simple and efficient manner, which can be routinely carried out in a refinery laboratory. Accordingly, the characterization method of this invention, using correlations developed by regression analysis, requires only usual tests that can be routinely carried out at a refinery laboratory.

In order to develop correlations for characterization of heavy residual petroleum mixtures, 367 oil samples were collected from operating refinery units over a one-year period. The samples were generally collected twice per week, however, during periods of significant crude feed changes, samples were collected daily for a five to seven day period. In this manner a broad spectrum of samples having a significant variation in properties was obtained. These samples, which include a range of oils including crude oil, virgin gas oil, light gas oil, vacuum bottoms and FCC recycle, were analyzed for carbon and hydrogen content using $C^{13}$ NMR, and proton NMR in conjunction with more common bulk property measurements including specific gravity, simulated distillation, and refractive index. These tests include:

Specific gravity

Simulated distillation Boiling Points

Refractive Index @ 68° F.

Total Hydrogen (NMR)

Aromatic Carbon ($C^{13}$ NMR)

Aromatic Hydrogen (NMR)

In order to develop the correlations for the model equations given above, the measured parameter values for the petroleum oils tested have the maximum and minimum values given in Table 1 below:

TABLE 1

Maximum and Minimum Values for Measured Oil Properties

| Property | Minimum | Maximum |
|---|---|---|
| Specific Gravity | 0.8838 | 1.0736 |
| Refractive Index @ 20° C. | 1.4897 | 1.6782 |
| Boiling Points, ° F. | | |
| Initial BP | 244 | 645 |
| 5% BP | 492 | 755 |
| 50% BP | 673 | 1014 |
| 95% BP | 872 | |
| % 1000° F.+ | 0 | 53.3 |
| Watson K | 10.3 | 12.1 |
| Total Hydrogen, wt. % | 8.2 | 13.0 |

TABLE 1-continued

Maximum and Minimum Values for Measured Oil Properties

| Property | Minimum | Maximum |
|---|---|---|
| Aromatic Carbon, wt. % | 10.7 | 62.9 |
| Aromatic Hydrogen, wt. % | 2.5 | 24.3 |

It was discovered that equations (1), (2), and (3) given above, which use refractive index and specific gravity in combination with the Watson K factor to include boiling points, is the best choice of correlation variables for characterizing the analyzed petroleum oils. Interestingly, a theoretical treatment exists which shows that each of these three selected correlation parameters will reach a constant value in considering an infinitely long $CH_2$ group in the liquid state. Smittenberg (see Smittenberg, Third World Petroleum Congress, The Hague, Section VI, 312–318, 1951) showed that each of these three parameters will reach a limiting value for an infinitely long $CH_2$ group in the liquid state. The values are 1.475 and 0.851 for refractive index and specific gravity respectively. Watson showed the limiting value to be 12.5 for the Watson K factor.

In examining a data set used in the above table that included 650° F. plus crude bottoms samples, gas oil samples, residual oil samples and FCC recycle samples, it was surprisingly discovered that the measured values for aromatic carbon, aromatic hydrogen and total hydrogen extrapolate to the limiting values of a corresponding property. Thus suggesting a predictive correlation equation having a fixed or zero intercept, if the measured bulk properties are adjusted by their respective limiting values.

The data below compares the standard error between measured and predicted values for the inventive method and the n-d-M and Totals methods, and indicates the advantage of the present invention.

Standard Errors of Regressions - Definition:

$$\sigma = \left[ \frac{1}{N} \cdot \sum_i (x_{icalc} - x_{imeas})^2 \right]^{1/2}$$

| Standard Errors for wt. % Aromatic Carbon | | | | |
|---|---|---|---|---|
| Group | # Samples | Phillips Model | n-d-Method | Total Method |
| Overall | 367 | 2.31 | 12.01 | 7.50 |

| Standard Errors for wt. % Hydrogen (by NMR) | | | |
|---|---|---|---|
| Group | # Samples | Phillips Model | Total Method |
| Overall | 367 | 0.28 | 0.78 |

| Standard Errors for wt. % Aromatic Hydrogen | | |
|---|---|---|
| Group | # Samples | Phillips Model |
| Overall | 367 | 1.78 |

The invention as described herein is an effective method for characterization of heavy petroleum oils. However, those skilled in the art will recognize that many modifications and variations of this invention are possible in light of the above teachings without departing from the spirit of the invention. It is to be understood that the present invention is not intended to be limited by the particular features described in the specification, but the concept of this invention is to be measured by the scope of the appended claims.

That which is claimed is:

1. A method for characterization of a hydrocarbon oil having an unknown composition, wherein said characterization is based on three measured bulk properties having limiting values for infinitely long carbon/hydrogen groups in the liquid state, said method comprising the following steps:

(a) calculating the aromatic carbon content of said heavy hydrocarbon oil using a model comprising a first equation based on measured bulk properties of said hydrogen oil including: refractive index and Watson K factor;

(b) calculating the aromatic hydrogen content of said heavy hydrocarbon oil using a model comprising a second equation based on measured bulk properties of said hydrogen oil including: refractive index and Watson K factor;

(c) calculating the total hydrogen content of said heavy hydrocarbon oil using a model comprising a third equation based on measured properties including: specific gravity and the Watson K factor; and (d) wherein said first, second and third equations include said limiting values for the respective measured property.

2. A method in accordance with claim 1, wherein said hydrocarbon oil includes petroleum oils having a boiling point up to 1400° F.

3. A method in accordance with claim 1, wherein said first, second and third equations are incorporated into a yields and properties prediction model for a fluidic catalytic cracking (FCC) unit.

4. A method in accordance with claim 1, wherein said first, second and third equations are as follows:

$$C_a = 134.4679[RI-1.4750] - 20.4858[K-12.5]$$

$$H_a = 333.471[RI-1.4750]^2 - 6.687[K-12.5]$$

$$H = -20.77[Sp.Gr.-0.8510] + 0.58[K-12.5] + 14.$$

where:

$C_a$=wt. % aromatic carbon $H_a$=wt. % aromatic hydrogen

H=wt. % total hydrogen

K=Watson K factor, i.e., $[(VABP(F)+460)^{1/3}]/Sp.Gr.$

RI=refractive index at 68° F.

SpGr.=specific gravity, density of oil at 60° F. relative to water at 60° F., and VABP = volume average of distillation curve boiling points at % off

= [10% + 30% + 50% + 70% + 90%]/5.

5. A method in accordance with claim 1, wherein said first, second and third equation are derived by correlating data obtained using a plurality of petroleum oil samples, and wherein said plurality of petroleum oil samples includes a broad spectrum of samples having significant variation in the measured properties.

6. A method in accordance with claim 5, wherein said petroleum oil samples are selected from the group of FCC feed stock material consisting of crude oil, virgin gas oil, light gas oil, fractionator bottoms, vacuum bottoms, and FCC recycle.

* * * * *